(12) United States Patent
Librizzi et al.

(10) Patent No.: US 7,157,414 B2
(45) Date of Patent: Jan. 2, 2007

(54) METHODS OF REDUCING IRRITATION IN PERSONAL CARE COMPOSITIONS

(75) Inventors: Joseph Librizzi, Hillsborough, NJ (US); Alison Protz, Huntsville, AL (US); Irina Ganopolsky, Lawrenceville, NJ (US); Russell Walters, Philadelphia, PA (US)

(73) Assignee: J&J Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 10/922,669

(22) Filed: Aug. 19, 2004

(65) Prior Publication Data

US 2005/0070453 A1    Mar. 31, 2005

Related U.S. Application Data

(63) Continuation-in-part of application No. 10/650,226, filed on Aug. 28, 2003, now Pat. No. 7,084,104, and a continuation-in-part of application No. 10/650,495, filed on Aug. 28, 2003, and a continuation-in-part of application No. 10/650,573, filed on Aug. 28, 2003, and a continuation-in-part of application No. 10/650,398, filed on Aug. 28, 2003, now abandoned.

(51) Int. Cl.
*C11D 9/32* (2006.01)
*C11D 1/12* (2006.01)
*C11D 3/37* (2006.01)
*A61K 8/23* (2006.01)

(52) U.S. Cl. .................. 510/127; 510/155; 510/158; 510/159; 510/426; 510/434; 510/470; 510/473; 510/476; 510/477; 510/492; 424/401; 424/487; 424/70.5; 424/70.16; 424/70.22; 424/70.24

(58) Field of Classification Search ............... 510/127, 510/155, 158, 159, 426, 434, 470, 473, 476, 510/477, 492; 424/401, 487, 70.5, 70.16, 424/70.22, 70.24
See application file for complete search history.

(56) References Cited

U.S. PATENT DOCUMENTS

| 4,110,263 A | 8/1978 | Lindemann et al. |
| 4,186,113 A | 1/1980 | Verdicchio et al. |
| 4,215,064 A | 7/1980 | Lindemann et al. |
| 4,233,192 A | 11/1980 | Lindemann et al. |
| 4,263,178 A | 4/1981 | Guth |

(Continued)

FOREIGN PATENT DOCUMENTS

DE    100 57 925 A1    5/2002

(Continued)

OTHER PUBLICATIONS

U.S. Appl. No. 10/922,668, (JBP5017CIP1), Johnson & Johnson Consumer Companies, Inc.

(Continued)

*Primary Examiner*—Brian P Mruk
(74) *Attorney, Agent, or Firm*—Brett Freeman

(57) ABSTRACT

Provided are methods of reducing the irritation associated with a personal care composition comprising an anionic surfactant, the methods comprising combining a hydrophobically-modified material capable of binding a surfactant thereto with an anionic surfactant to produce a reduced irritation personal care composition, and methods of using such compositions to cleanse the hair or skin with reduced irritation.

15 Claims, 3 Drawing Sheets

U.S. PATENT DOCUMENTS

| | | | |
|---|---|---|---|
| 4,372,869 | A | 2/1983 | Lindemann et al. |
| 4,380,637 | A | 4/1983 | Lindemann et al. |
| 4,382,036 | A | 5/1983 | Lindemann et al. |
| 4,443,362 | A | 4/1984 | Guth et al. |
| 4,617,414 | A | 10/1986 | Lukenbach et al. |
| 4,726,915 | A | 2/1988 | Verdicchio |
| 5,373,044 | A | 12/1994 | Adams et al. |
| 5,661,189 | A | 8/1997 | Grieveson et al. |
| 5,876,705 | A | 3/1999 | Uchiyama et al. |
| 6,001,344 | A | 12/1999 | Villa et al. |
| 6,172,019 | B1 | 1/2001 | Dehan et al. |
| 6,433,061 | B1 | 8/2002 | Marchant et al. |
| 6,642,198 | B1 * | 11/2003 | Pflederer et al. ............ 510/434 |
| 6,737,394 | B1 * | 5/2004 | Shana'a et al. ............ 510/417 |
| 2003/0026775 | A1 | 2/2003 | Marchesi et al. |
| 2003/0108578 | A1 | 6/2003 | Maubru |
| 2003/0147827 | A1 * | 8/2003 | Decoster et al. ......... 424/70.12 |
| 2004/0001792 | A1 | 1/2004 | Biatry |
| 2004/0042990 | A1 | 3/2004 | Biatry |
| 2004/0047824 | A1 | 3/2004 | Biatry |
| 2004/0052739 | A1 | 3/2004 | Biatry |
| 2004/0091441 | A1 | 5/2004 | Heike et al. |
| 2004/0175342 | A1 | 9/2004 | Biatry |

FOREIGN PATENT DOCUMENTS

| | | |
|---|---|---|
| EP | 1 374 852 A1 | 1/2004 |
| WO | WO 03/074021 A1 | 9/2003 |
| WO | WO 03/084499 A2 | 10/2003 |
| WO | WO 04/006870 A2 | 1/2004 |

OTHER PUBLICATIONS

U.S. Appl. No. 10/959,272, (JBP5017CIP2), Johnson & Johnson Consumer Companies, Inc.
European Search Report dated Dec. 21, 2004 for EP appln. 04254988.1.
European Search Report dated Dec. 21, 2004 for EP appln. 04254989.9.
European Search Report dated Dec. 21, 2004 for EP appln. 04254987.3.
European Search Report dated Dec. 21, 2004 for EP appln. 04254990.7.
International Search Report dated Dec. 17, 2004 for PCT/US04/27317.
Bernhofer, et al., Toxicology in Vitro, 219-229 (1999).
Carbopol® Aqua SF-1 Polymer, Brilliant Gold Pearlized 2-In-1 Conditioning Shampoo Formulation, Noveon, Inc. CASF1-001, Dec. 2000.
Carbopol® Aqua SF-1 Polymer, Pearlized 2-in-1 Conditioning Shampoo formulation, Noveon, Inc., CASF1-002, Nov. 19, 2001.
Carbopol® Aqua SF-1 Polymer, Clear Shampoo Formulation, Noveon, Inc., CASF1-003, Dec. 2000.
Carbopol® SF-1 Polymer, Bath Gel with Vitamin E Moisturizing Beads Formulation, Noveon, Inc., CASF1-004, Dec. 2000.
Carbopol® Aqua SF-1 Polymer, Pearlized Mild Body Wash Formulation, Noveon, Inc., CASF1-005, Nov. 19, 2001.
Carbopol® Aqua SF-1 Polymer, Clear Bath Gel (High Betaine) Formulation, Noveon, Inc., CASF1-006, Dec. 2000.
Carbopol® Aqua SF-1 Polymer, Anti-Dandruff Shampoo Formulation, Noveon, Inc., CASF1-007, Dec. 2000.
Carbopol® Aqua SF-1 Polymer, Clear Shampoo/Bath Gel with Beads Formulation, Noveon, Inc., CASF1-008, Mar. 29, 2002.
Carbopol® Aqua SF-1 Polymer, Salicylic Acid Shampoo Formulation, Noveon, Inc., CASF1-009, Dec. 2000.
Carbopol® Aqua SF-1 Polymer, Salicylic Acid Facial Scrub Formulation, Noveon, Inc., CASF1-010, Feb. 25, 2002.
Carbopol® Aqua SF-1 Polymer, Temporary Hair Color shampoo (Medium Brown) Formulation, Noveon, Inc., CASF1-011, Dec. 2000.
Carbopol® Aqua SF-1 Polymer, Antibacterial Liquid Hand Soap with suspended Beads Formulation, Noveon, Inc., CASF1-012, Dec. 2000.
Carbopol® Aqua SF-1 Polymer, Clear Facial Cleanser Formulation, Noveon, Inc., CASF1-013, Dec. 2000.
Carbopol® Aqua SF-1 Polymer, Clear Hydrating Body Wash with Susepnded Beads Formulation, Noveon, Inc., CASF1-014, Nov. 19, 2001.
Carbopol® Aqua SF-1 Polymer, Sprayable d-Limonene Waterless Hand Cleaner Formulation, Noveon, Inc., CASF1-015, Jan. 2001.
Carbopol® Aqua SF-1 Polymer, Body Lotion Formulation, Noveon, Inc., CASF1-016, Dec. 2000.
Carbopol® Aqua SF-1 Polymer, Facial Cream Formulation, Noveon, Inc., CASF1-017, Dec. 2000.
Carbopol® Aqua SF-1 Polymer, Alpha Hydroxy Acid Cream Formulation, Noveon, Inc., CASF1-018, Dec. 2000.
Carbopol® Aqua SF-1 Polymer, Pearlized 3-In-1 Conditioning Shampoo Formulation, Noveon, Inc., CASF1-019, Nov. 19, 2001.
Carbopol® Aqua SF-1 Polymer, Clear Shampoo with Microcapsules Formulation, Noveon, Inc., CASF1-020, Dec. 2000.
Carbopol® Aqua SF-1 Polymer, Clear Baby Shampoo Formulation, Noveon, Inc., CASF1-021, Dec. 2000.
Carbopol® Aqua SF-1 Polymer, Economy Pearlized 3-in-1 Conditioning Shampoo Formulation, Noveon, Inc., CASF1-022, Jan. 2001.
Clear Conditioning Shampoo Using Ultrasil™ Q-Plus and Ultrasil™ A-23 Silicones, Noveon, Inc., SIL-019, Dec. 12, 2002.
Clear Bath Gel (High Betaine) Using Carbopol® Aqua SF-1 Polymer, Noveon, Inc., CASF1-024EU, Feb. 10, 2003.
Clear Shampoo/Bath Gel with Beads Using Carbopol® Aqua SF-1 Polymer, Noveon, Inc., CASF1-025EU, Feb. 26, 2003.
Brilliant Gold Pearlized 2-in-1 Conditioning Shampoo Using Carbopol® Aqua SF-1 Polymer, Noveon, Inc., CASF1-026EU, Feb. 26, 2003.
Ethnic Hair Moisturizing Cream With Ultracas™ G-20, Noveon, Inc., SIL-0002, Jun. 28, 2001.
Antibacterial Hand Wash with Moisturizers Using Ultrasil™ DW-18 Silicone, Noveon, Inc., SIL-0005, Mar. 1, 2002.
Mild Conditioning Cream Shampoo, Noveon, Inc., SIL-0017, Dec. 12, 2002.
Moisturizing Shampoo for Ethnic Hair, Noveon, Inc., SIL-0020, Feb. 26, 2003.
Aveeno® Stress Relief Foaming Bath Formulation, Johnson & Johnson Consumer Companies, Inc., 2003.
Aveeno® Daily Moisturizing Foaming Bath Formulation, Johnson & Johnson Consumer Companies, Inc., 2003.
Aveeno® Positively Radiant™ Cleanser Formulation, Johnson & Johnson Consumer Companies, Inc., 2003.
Johnson's® Softwash™ Baby Shampoo Formulation, Johnson & Johnson Consumer Companies, Inc., 2002.
Johnson's® Softwash™ Baby Wash Formulation, Johnson & Johnson Consumer Companies, Inc., 2002.
Johnson's® Soothing Skin Baby Bath Formulation, Johnson & Johnson Consumer Companies, Inc., 2001.
Invittox Protocol No. 86, "The Trans-Epithelial Permeability (TEP) Assay," (May 1994).
Moore, et al., Challenging the surfactant monomer skin penetration model: Penetration of sodium dodecyl sulfate micelles into the epidermis (Journal of Cosmetic Science), Nov. 15, 2002, pp. 29-45.
Moore, et al., Penetration of mixed micelles into the epidermis: Effect of mixing sodium dodecyl sulfate with dodecyl hexa (ethylene oxide) (Journal of Cosmetic Science), 54, 2003, pp. 143-159.

* cited by examiner

METHODS OF REDUCING IRRITATION IN PERSONAL CARE COMPOSITIONS

CROSS-REFERENCES TO RELATED APPLICATIONS

This application is a continuation-in-part of U.S. application Ser. Nos. 10/650,226 now U.S. Pat. No. 7,084,104, Ser. No. 10/650,495 pending, Ser. No. 10/650,573 pending, and Ser. No. 10/650,398 now abandoned, each of which was filed on Aug. 28, 2003. Each of the aforementioned applications is incorporated herein by reference.

FIELD OF INVENTION

The present invention relates to methods for reducing the irritation characteristics associated with a variety of personal care compositions, and methods of using such compositions.

DESCRIPTION OF THE RELATED ART

Synthetic detergents, such as cationic, anionic, amphoteric, and non-ionic surfactants, are used widely in a variety of detergent and cleansing compositions. For many of such compositions, including, for example, shampoos, it is desirable to use a surfactant which imparts or provides to the composition, when incorporated therein, relatively high foam volume and foam stability. It is generally recognized that such foam properties are directly related to the perceived efficiency with which a shampoo cleans the hair. That is, the greater the volume of foam produced and the greater the stability of the foam, the more efficient the perceived cleansing action of the shampoo.

Anionic surfactants tend to exhibit superior cleansing and foaming properties, and thus are incorporated into many personal cleansing compositions. However, these anionic surfactants also tend to be very irritating to the skin and eyes. To produce more mild cleansing compositions, it is well-known to replace some of the anionic surfactant therein with other surfactants, such as nonionic and/or amphoteric surfactants. See, e.g. U.S. Pat. No. 4,726,915. Another approach to producing mild cleansing compositions is to associate the anionic surfactants with amphoteric or cationic compounds in order to yield surfactant complexes. See, e.g., U.S. Pat. Nos. 4,443,362; 4,726,915; 4,186,113; and 4,110,263. Disadvantageously, mild cleansing compositions produced via both of such methods tend to suffer from poor foaming and cleansing performance.

In addition, recent literature, Moore, P.; Shiloach, A.; Puvvada, S.; Blankschtein, D. *Journal of Cosmetic Science*, 54, 2003, 143–159 ("Moore et al.") has described the addition of polyethylene oxide (PEO) to a solution of water and relatively low concentrations (significantly below the levels typical of personal care cleansing compositions) of sodium dodecyl sulfate (SDS), a cleansing surfactant, to reduce the penetration of SDS into the epidermis skin. Moore et al. postulates that by binding free micelles of the surfactant thereto, the PEO forms larger micelles with the SDS, as compared to the free SDS micelles, which larger micelles are not able to penetrate the stratum cornea as readily as the smaller free micelles. In this manner, Moore et al. asserts that surfactant penetration into the skin is mitigated, and that this reduced surfactant penetration may lead to reduced skin irritation.

Nevertheless, applicants have recognized that PEO does not sufficiently bind surfactant thereto, and does not provide a significant or sufficient reduction in irritation, when added to compositions comprising levels of surfactant higher than those disclosed in Moore et al. Because conventional personal care compositions tend to comprise levels of surfactant higher than those disclosed in Moore et al., applicants have recognized that the teachings of Moore et al. do not significantly overcome the disadvantages associated with other methods of mitigating irritation in personal care compositions.

In light of the above, applicants have recognized the need for methods of producing personal care compositions having reduced irritation to the skin and/or eye without adversely impacting the foam properties and/or other aesthetics associated therewith.

SUMMARY OF THE INVENTION

The present invention provides methods of reducing the irritation associated with a variety of personal care compositions which methods overcome the disadvantages of the prior art. In particular, according to certain preferred embodiments of the present invention, applicants have discovered advantageously that hydrophobically-modified materials capable of binding surfactant thereto can be combined with anionic surfactants to produce personal care compositions exhibiting relatively low irritation to the skin and/or eyes, and/or relatively high-foaming/foam stability properties.

One aspect of the present invention provides for methods of reducing the irritation associated with a personal care composition comprising an anionic surfactant, the method comprising combining a hydrophobically-modified material capable of binding a surfactant thereto with an anionic surfactant to produce a reduced irritation personal care composition comprising from about 3.5 to less than 7.5 weight percent, based on the total weight of the reduced irritation composition, of anionic surfactant.

According to another aspect of the present invention, provided are compositions produced according to the present invention.

According to yet another aspect of the present invention, provided are methods of cleansing skin or hair with reduced irritation thereto comprising the step of contacting the skin or hair of a mammal with a reduced irritation composition comprising an anionic surfactant and a hydrophobically modified material capable of binding a surfactant thereto.

DESCRIPTION OF PREFERRED EMBODIMENTS

Figure 1:
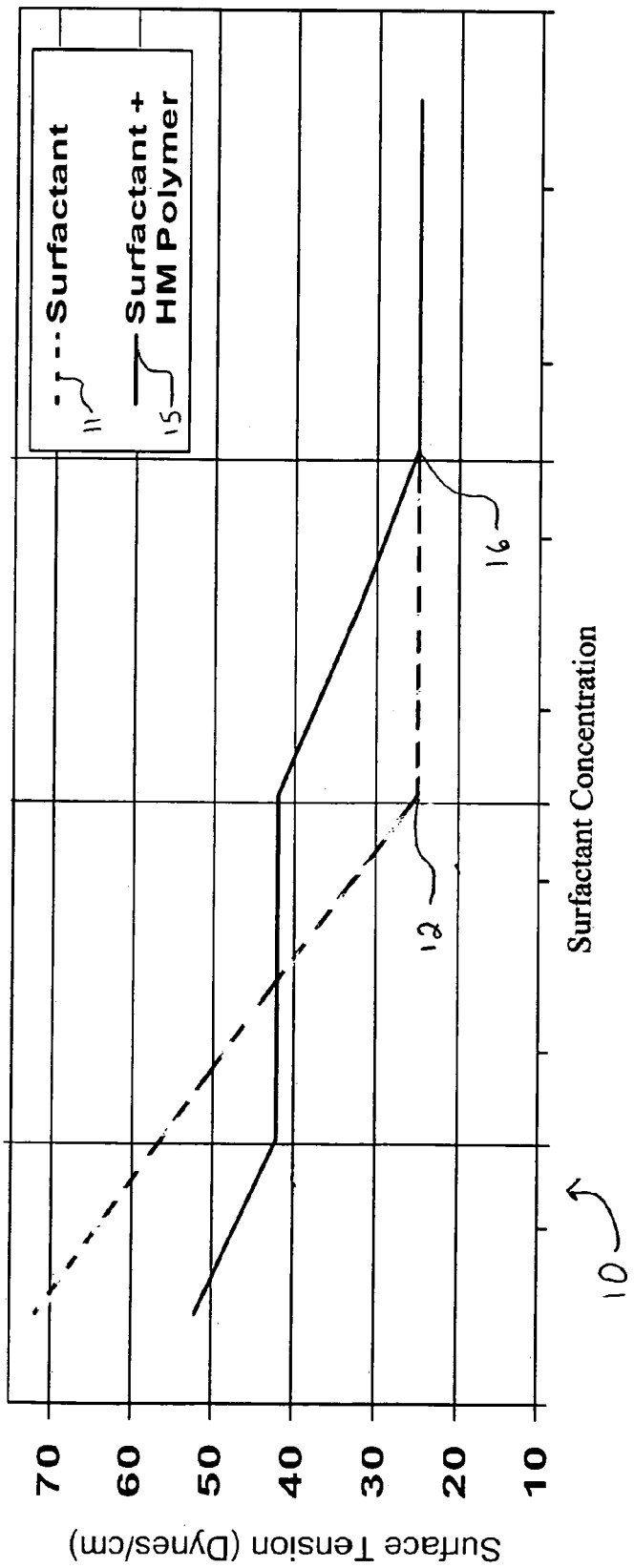
FIG. 1 is a graphical depiction of the idealized tensiometry data associated with the addition of anionic surfactant to two solutions.

All percents described herein are weight-by-weight percent based on the total weight of composition, unless otherwise indicated.

With regard to reduced irritation, applicants have recognized that the "TEP value" associated with a particular composition, which value is measured conventionally via the Trans-Epithelial Permeability Test ("TEP Test") as set forth in the Invittox Protocol Number 86 (May 1994) incorporated herein by reference and described in further detail in the Examples below, has a direct correlation to the irritation to the skin and/or eyes associated with the composition. More specifically, a higher TEP value of a composition tends to indicate less irritation to the skin and eyes associated therewith as compared to a composition having a lower TEP value, which composition tends to cause higher levels of irritation to the skin and/or eyes. Applicants have recognized that the present methods are suitable for producing personal care compositions having surprisingly high TEP values/lower irritation associated therewith. For example, in certain embodiments, the present methods produce compositions having a TEP value of at least about 1.5 or greater. In certain more preferred embodiments, the composition produced according to the present methods exhibit a TEP value of at least about 2 or greater, more preferably, at least about 2.5 or greater, even more preferably, at least about 3 or greater, and still more preferably, at least about 3.5 or greater. In certain particularly preferred embodiments, the compounds exhibit a TEP value of at least about 4.0 or greater, and even more preferably, about 4.5 or greater.

Furthermore, to determine when, and to express the degree to which, a composition comprising an anionic surfactant and a hydrophobically-modified material produced via the present methods exhibits reduced irritation in comparison to a comparable composition free of the hydrophobically-modified material, applicants herein define the term "Delta TEP" of a composition of the present invention as the value obtained by: (a) measuring the TEP values of: (i) the composition of the present invention comprising an anionic surfactant and hydrophobically-modified material and (ii) the comparable composition for such composition; and (b) subtracting the TEP value of the comparable composition from the TEP value for the anionic surfactant/hydrophobically-modified material composition. As used herein, the "comparable composition" of a particular composition comprising anionic surfactant and hydrophobically-modified material means a composition which consists of the same components in the same relative weight percents as the anionic surfactant/hydrophobically-modified material composition with the exception that the hydrophobically-modified polymer of the anionic surfactant/hydrophobically-modified material composition is replaced in the comparable composition with the same relative weight percent of water. For example, the comparable composition for an anionic surfactant/hydrophobically-modified composition consisting of 7% anionic surfactant, 15% amphoteric surfactant, 5% hydrophobically-modified polymer, 5% glycerin, and 68% water (wherein all percents are by weight based on the total weight of the composition) is a composition consisting of 7% anionic surfactant, 15% amphoteric surfactant, 5% glycerin, and 73% water. In addition, as described hereinbelow, the composition of Example 10 is a comparable composition for the anionic surfactant/hydrophobically-modified polymer compositions formed in Examples 11–15.

In light of the above, as used herein the term "reduced irritation composition" refers generally to a composition comprising an anionic surfactant and one or more hydrophobically-modified materials capable of binding surfactant thereto, which composition has a positive Delta TEP value (i.e. the composition has higher TEP value than its comparable composition), measured via the Invittox Protocol incorporated herein. Certain preferred reduced irritation compositions of the present invention include those having a Delta TEP of at least about +0.5. Certain more preferred reduced irritation compositions include those having a Delta TEP of at least about +0.75, and more preferably at least about +1. Certain particularly preferred reduced irritation compositions include those having a Delta TEP that is at least about +1.2, more preferably at least about +1.5, and more preferably at least about +1.8.

As used herein, the term "hydrophobically-modified material" refers generally to any material having one or more hydrophobic moieties attached thereto or incorporated therein. Examples of certain types of preferred hydrophobically-modified materials include hydrophobically-modified polymers. Such polymers may be formed, for example, by polymerizing one or more hydrophobic monomers and, optionally, one or more co-monomers, to form a polymer having hydrophobic moieties incorporated therein, and/or also by reacting polymer materials with compounds comprising hydrophobic moieties to attach such compounds to the polymers. Certain hydrophobically-modified polymers and methods of making such polymers are described in U.S. Pat. No. 6,433,061, issued to Marchant et al. and incorporated herein by reference.

Any of a variety of hydrophobically-modified materials capable of binding surfactant thereto are suitable for use in the present invention. Although applicants do not wish to be bound by or to any particular theory of operation, it is believed that the hydrophobically-modified materials suitable for use in the instant methods act to reduce the irritation associated with personal care compositions, at least in part, by binding surfactant (free (unbound) surfactant molecules and/or, especially, surfactant free (unbound) micelles) thereto to reduce the concentration of irritation-causing free micelles available in the composition to irritate the skin and/or eyes. That is, applicants have recognized that the relative amounts of surfactant free micelles contained in a particular composition affect the relative irritation to the skin and/or eyes associated with that composition, wherein higher amounts of free micelles tend to cause higher levels of irritation and lower levels of free micelles tends to cause less irritation. By binding surfactant and/or surfactant micelles thereto, the hydrophobically-modified materials reduce the concentration of unbound surfactant micelles in a composition and allow for a higher concentration of surfactant to be added to the composition before free mioelles are formed and/or before a particular level of irritation is achieved. This desirable shift in the concentration of surfactant required prior to the formation of free micelles is illustrated further in FIG. 1.

FIG. 1 is a graph 10 showing the idealized surface tension data curves associated with the addition of anionic surfactant to two compositions, a composition comprising a hydrophobically-modified material of the present invention and a comparable composition composition free of hydrophobically-modified material. Curve 11 shows the change in surface tension, measured via conventional tensiometry techniques. (examples of which are described hereinbelow), of a composition free of hydrophobically-modified material as increasing levels of anionic surfactant are added thereto. Curve 15 shows the change in surface tension of a composition comprising hydrophobically-modified material as increasing levels of anionic surfactant are added thereto. In curve 11, as surfactant is added to solution, the surfactant tends to populate the liquid/air interface, thus reducing the surface tension of the solution, until essentially the entire surface area is filled. After this point, hereinafter the "critical micelle concentration (CMC)" of surfactant, point 12, essentially all surfactant added to the composition forms free micelles in solution, which formation does not have an appreciable affect on the surface tension of the solution, but tends to increase the irritation associated with the composition. By comparison, as shown in curve 15, as anionic surfactant is added to a solution comprising a hydrophobically-modified material, the surfactant both aligns itself on the liquid/air interface and binds to the hydrophobically-modified material until the CMC, point 16, shifted to a significantly higher surfactant concentration as compared to curve 11, at which point the surfactant added tends to form free micelles.

In light of the above, applicants have recognized that one measure of the efficacy of a particular hydrophobically-modified material in binding surfactant thereto may be expressed as the "Delta CMC" achieved by combining the hydrophobically-modified material with an anionic surfactant to form a reduced irritation composition. A "Delta CMC" as used herein is defined as the number obtained by: (a) determining the CMC for: (i) a particular composition of the present invention comprising anionic surfactant and hydrophobically-modified material, and (ii) the comparable composition of the composition in (i), which CMC values are determined using the Reverse Titration Tensiomtry Test procedures defined in the Examples below; and (b) subtracting the CMC value obtained for composition (ii) from the value obtained for composition (i). In certain embodiments, it is preferred to select a hydrophobically-modified material for use in the present methods such that the Delta CMC associated with the resulting reduced irritation composition is a positive value. In certain more preferred embodiments, the hydrophobically-modified material is selected to achieve a reduced irritation composition having a Delta CMC of about +16 or greater, more preferably, about +80 or greater, and even more preferably of about +300 or greater.

Examples of hydrophobically-modified materials capable of binding a surfactant thereto and suitable for use in the present methods include hydrophobically-modified polymers, for example, hydrophobically-modified acrylic polymers, as well as, hydrophobically-modified cellulosics, hydrophobically-modified starches, combinations of two or more thereof, and the like.

Hydrophobically-modified acrylic polymers suitable for use in the present invention may be in the form of random, block, star, graft copolymers, and the like. In certain embodiments, the hydrophobically-modified acrylic polymers are crosslinked, anionic acrylic copolymers. Such copolymers may be synthesized from at least one acidic monomer and at least one hydrophobic ethylenically unsaturated monomer. Examples of suitable acidic monomers include those ethylenically unsaturated acid monomers that may be neutralized by a base. Examples of suitable hydrophobic ethylenically unsaturated monomers include those that contain a hydrophobic chain having a carbon chain length of at least 3 carbon atoms.

In another embodiment, the hydrophobically-modified, crosslinked, anionic acrylic copolymer includes those compositions derived from at least one unsaturated carboxylic acid monomer; at least one hydrophobic monomer; a hydrophobic chain transfer agent comprising alkyl mercaptans, thioesters, amino acid-mercaptan-containing compounds or peptide fragments, or combinations thereof; a cross-linking agent; and, optionally, a steric stabilizer; wherein the amount of said unsaturated carboxylic acid monomer is from about 60% to about 98% by weight based upon the total weight of said unsaturated monomers and said hydrophobic monomer, as set forth in U.S. Pat. No. 6,433,061, which is incorporated by reference herein. In one embodiment, the polymer is an acrylates copolymer that is commercially available from Noveon, Inc. under the tradename, "Carbopol Aqua SF-1."

Any of a variety of hydrophobically-modified cellulosics or starches are suitable for use in the present invention. Examples of suitable hydrophobically-modified cellulosics include hydrophobically-modified hydroxyethyl cellulose (available commercially, for example, from Hercules Inc. (Wilmington, Del.) as "Natrosol Plus"), and the like. Examples of suitable hydrophobically-modified starches include hydrophobically-modified hydroxylpropyl starch phosphate (available commercially, for example, from National Starch (Bridgewater, N.J.) as "Structure XL"), and the like.

In certain preferred embodiments of the present invention, the hydrophobically modified materials comprise hydrophobically-modified acrylic polymers, more preferably hydrophobically-modified crosslinked, anionic acrylic copolymers.

Any of a variety of anionic surfactants may be combined with a hydrophobically-modified material to form a reduced irritation composition according to preferred embodiments of the present methods. According to certain embodiments, suitable anionic surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. Examples of certain preferred anionic surfactants include:

alkyl sulfates of the formula

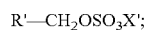
$R'$—$CH_2OSO_3X'$;

alkyl ether sulfates of the formula

$R'(OCH_2CH_2)_vOSO_3X'$;

alkyl monoglyceryl ether sulfates of the formula

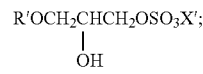
$R'OCH_2CHCH_2OSO_3X'$;
$|$
$OH$ alkyl monoglyceride sulfates of the formula

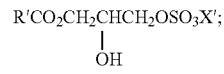
$R'CO_2CH_2CHCH_2OSO_3X'$;
$|$
$OH$ alkyl monoglyceride sulfonates of the formula

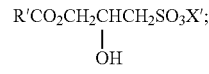
$R'CO_2CH_2CHCH_2SO_3X'$;
$|$
$OH$ alkyl sulfonates of the formula

$R'$—$SO_3X'$;

alkylaryl sulfonates of the formula

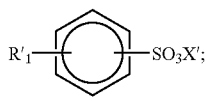

alkyl sulfosuccinates of the formula: alkyl ether sulfosuccinates of the formula:

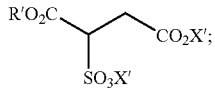

alkyl sulfosuccinamates of the formula:

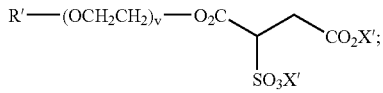

alkyl sulfosuccinamates of the foruula:

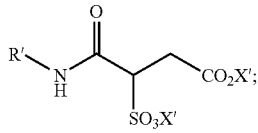

alkyl amidosulfosuccinates of the formula

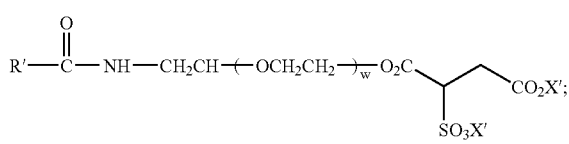

alkyl carboxylates of the formula:

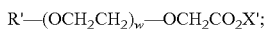

alkyl amidoethercarboxylates of the formula:

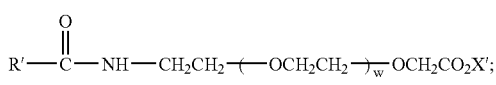

alkyl succinates of the formula:

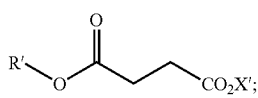

fatty acyl sarcosinates of the formula:

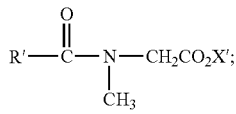

fatty acyl amino acids of the formula:

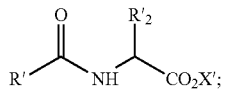

fatty acyl taurates of the formula:

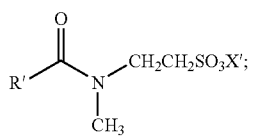

fatty alkyl sulfoacetates of the formula:

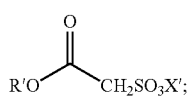

alkyl phosphates of the formula:

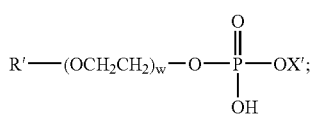

wherein
R' is an alkyl group having from about 7 to about 22, and preferably from about 7 to about 16 carbon atoms,
$R'_1$ is an alkyl group having from about 1 to about 18, and preferably from about 8 to about 14 carbon atoms,
$R'_2$ is a substituent of a natural or synthetic l-amino acid,
X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and
v is an integer from 1 to 6;
w is an integer from 0 to 20;
and mixtures thereof.

According to certain embodiments, the anionic surfactant of the present invention preferably comprises one or more alkyl ether sulfates, or mixtures thereof. In certain more preferred embodiments, the anionic surfactant of the present invention comprises sodium trideceth sulfate. Sodium trideceth sulfate is the sodium salt of sulfated ethoxylated tridecyl alcohol that conforms generally to the following formula, $C_{13}H_{27}(OCH_2CH_2)_nOSO_3Na$, where n has a value between 1 and 4, and is commercially available from Stepan Company of Northfield, Ill. under the tradename, "Cedapal TD-403M." Applicants have recognized that sodium trideceth sulfate can be used to particular advantage to obtain compositions having significantly reduced irritation associated therewith according to the present invention.

Any amounts of hydrophobically-modified materials and anionic surfactants suitable to produce a reduced irritation composition may be combined according to the present methods. According to certain embodiments, sufficient hydrophobically-modified material is used to produced a reduced irritation composition comprising from greater than zero to about 8% by weight of active hydrophobically-modified material in the composition. Preferably, sufficient hydrophobically-modified material is used to produce a reduced irritation composition comprising from about 0.01 to about 5%, more preferably from about 0.01 to about 4%, even more preferably from about 0.1 to about 4% and even more preferably from about 0.1 to about 3% of active hydrophobically-modified material in the composition. The amount of anionic surfactant used in the present invention is preferably an amount sufficient to produce a reduced irritation composition comprising from about 0.1 to about 12.5%, more preferably from about 0.5 to about 8.5%, even more preferably from about 1 to about 8% of total active anionic surfactant in the composition. In certain other preferred embodiments, the amount of active anionic surfactant is an amount sufficient to produce a reduced irritation composition comprising from about 3.5 to about 7.3%, more preferably from 3.5% or greater to 7.3% or less, more preferably from 3.5% to 7%, and even more preferably from 4% to 7% of total active anionic surfactant in the composition.

The hydrophobically-modified material and anionic surfactant may be combined according to the present invention via any conventional methods of combining two or more fluids. For example, one or more compositions comprising, consisting essentially of, or consisting of at least one hydrophobically-modified material and one or more compositions comprising, consisting essentially of, or consisting of at least one anionic surfactant may be combined by pouring, mixing, adding dropwise, pipetting, pumping, and the like, one of the compositions comprising hydrophobically-modified material or anionic surfactant into or with the other in any order using any conventional equipment such as a mechanically stirred propeller, paddle, and the like. According to certain embodiments, the combining step comprises combining a composition comprising anionic surfactant into or with a composition comprising hydrophobically-modified material. According to certain other embodiments, the combining step comprises combining a composition comprising hydrophobically-modified material into or with a composition comprising anionic surfactant.

The reduced irritation compositions produced, as well as any of the compositions comprising hydrophobically-modified material or anionic surfactant that are combined in the combining step according to the present methods may further comprise any of a variety of other components nonexclusively including one or more nonionic, amphoteric, and/or cationic surfactants, pearlescent or opacifying agents, thickening agents, secondary conditioners, humectants, chelating agents, and additives which enhance the appearance, feel and fragrance of the compositions, such as colorants, fragrances, preservatives, pH adjusting agents, and the like.

Any of a variety of nonionic surfactants are suitable for use in the present invention. Examples of suitable nonionic surfactants include, but are not limited to, fatty alcohol acid or amide ethoxylates, monoglyceride ethoxylates, sorbitan ester ethoxylates alkyl polyglycosides, mixtures thereof, and the like. Certain preferred nonionic surfactants include polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester. Examples of such preferred polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Del. under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Del. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl gluocosides comprise from about 1 to about 6 glucose residues per molecule of alkyl glucoside. A preferred glucoside is decyl glucoside, which is the condensation product of decyl alcohol with a glucose polymer and is available commercially from Henkel Corporation of Hoboken, N.J. under the tradename, "Plantaren 2000."

As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Examples of amphoteric surfactants suitable for use in the present invention include, but are not limited to, amphocarboxylates such as alkylamphoacetates (mono or di); alkyl betaines; amidoalkyl betaines; amidoalkyl sultaines; amphophosphates; phosphorylated imidazolines such as phosphobetaines and Pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof.

Examples of suitable amphocarboxylate compounds include those of the formula:

wherein
A is an alkyl or alkenyl group having from about 7 to about 21, e.g. from about 10 to about 16 carbon atoms;
x is an integer of from about 2 to about 6;
$R_5$ is hydrogen or a carboxyalkyl group containing from about 2 to about 3 carbon atoms;
$R_6$ is a hydroxyalkyl group containing from about 2 to about 3 carbon atoms or is a group of the formula:

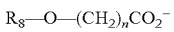

wherein
$R_8$ is an alkylene group having from about 2 to about 3 carbon atoms and n is 1 or 2; and
$R_7$ is a carboxyalkyl group containing from about 2 to about 3 carbon atoms;

Examples of suitable alkyl betaines include those compounds of the formula:

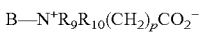

wherein
B is an alkyl or alkenyl group having from about 8 to about 22, e.g., from about 8 to about 16 carbon atoms;
$R_9$ and $R_{10}$ are each independently an alkyl or hydroxyalkyl group having from about 1 to about 4 carbon atoms; and
p is 1 or 2.

A preferred betaine for use in the present invention is lauryl betaine, available commercially from Albright & Wilson, Ltd. of West Midlands, United Kingdom as "Empigen BB/J."

Examples of suitable amidoalkyl betaines include those compounds of the formula:

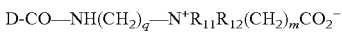

wherein
D is an alkyl or alkenyl group having from about 7 to about 21, e.g. from about 7 to about 15 carbon atoms;
$R_{11}$ and $R_{12}$ are each independently an alkyl or Hydroxyalkyl group having from about 1 to about 4 carbon atoms;
q is an integer from about 2 to about 6; and m is 1 or 2.

One amidoalkyl betaine is cocamidopropyl betaine, available commercially from Goldschmidt Chemical Corporation of Hopewell, Va. under the tradename, "Tegobetaine L7."

Examples of suitable amidoalkyl sultaines include those compounds of the formula

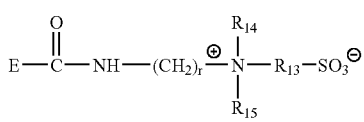

wherein
E is an alkyl or alkenyl group having from about 7 to about 21, e.g. from about 7 to about 15 carbon atoms;
$R_{14}$ and $R_{15}$ are each independently an alkyl, or hydroxyalkyl group having from about 1 to about 4 carbon atoms;

r is an integer from about 2 to about 6; and
$R_{13}$ is an alkylene or hydroxyalkylene group having from about 2 to about 3 carbon atoms;

In one embodiment, the amidoalkyl sultaine is cocamidopropyl hydroxysultaine, available commercially from Rhone-Poulenc Inc. of Cranbury, N.J. under the tradename, "Mirataine CBS."

Examples of suitable amphophosphate compounds include those of the formula:

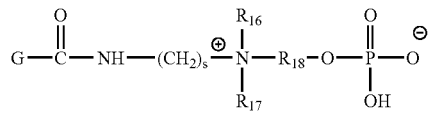

wherein
G is an alkyl or alkenyl group having about 7 to about 21, e.g. from about 7 to about 15 carbon atoms;
s is an integer from about 2 to about 6;
$R_{16}$ is hydrogen or a carboxyalkyl group containing from about 2 to about 3 carbon atoms;
$R_{17}$ is a hydroxyalkyl group containing from about 2 to about 3 carbon atoms or a group of the formula:

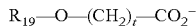

wherein
$R_{19}$ is an alkylene or hydroxyalkylene group having from about 2 to about 3 carbon atoms and t is 1 or 2; and
$R_{18}$ is an alkylene or hydroxyalkylene group having from about 2 to about 3 carbon atoms.

In one embodiment, the amphophosphate compounds are sodium lauroampho PG-acetate phosphate, available commercially from Mona Industries of Paterson, N.J. under the tradename, "Monateric 1023," and those disclosed in U.S. Pat. No. 4,380,637, which is incorporated herein by reference.

Examples of suitable phosphobetaines include those compounds of the formula:

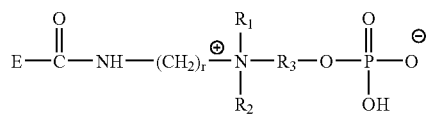

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

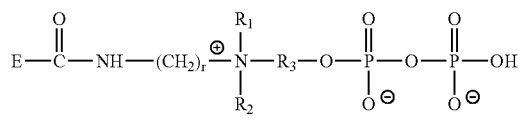

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

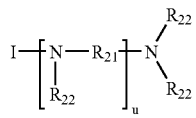

wherein
I is an alkyl or alkenyl group containing from about 8 to about 22, e.g. from about 8 to about 16 carbon atoms;
$R_{22}$ is a carboxyalkyl group having from about 2 to about 3 carbon atoms;
$R_{21}$ is an alkylene group having from about 2 to about 3 carbon atoms and
u is an integer from about 0.1 to about 4.

Classes of cationic surfactants that are suitable for use in this invention include alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

Any of a variety of commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent may be present in an amount, based upon the total weight of the composition, of from about 1 percent to about 10 percent, e.g. from about 1.5 percent to about 7 percent or from about 2 percent to about 5 percent. Examples of suitable pearlescent or opacifying agents include, but are not limited to mono or diesters of (a) fatty acids having from about 0.16 to about 22 carbon atoms and (b) either ethylene or propylene glycol; mono or diesters of (a) fatty acids having from about 16 to about 22 carbon atoms (b) a polyalkylene glycol of the formula: HO-(JO)$_a$—H, wherein J is an alkylene group having from about 2 to about 3 carbon atoms; and a is 2 or 3; fatty alcohols containing from about 16 to about 22 carbon atoms; fatty esters of the formula: KCOOCH$_2$L, wherein K and L independently contain from about 15 to about 21 carbon atoms; inorganic solids insoluble in the shampoo composition, and mixtures thereof.

The pearlescent or opacifying agent may be introduced to the mild cleansing composition as a pre-formed, stabilized aqueous dispersion, such as that commercially available from Henkel Corporation of Hoboken, N.J. under the tradename, "Euperlan PK-3000." This material is a combination of glycol distearate (the diester of ethylene glycol and stearic acid), Laureth-4 (CH$_3$(CH$_2$)$_{10}$CH$_2$(OCH$_2$CH$_2$)$_4$OH) and cocamidopropyl betaine and may be in a weight percent ratio of from about 25 to about 30: about 3 to about 15: about 20 to about 25, respectively.

Any of a variety of commercially available thickening agents, which are capable of imparting the appropriate viscosity to the personal cleansing compositions are suitable for use in this invention. If used, the thickener should be present in the shampoo compositions in an amount sufficient to raise the Brookfield viscosity of the composition to a value of between about 500 to about 10,000 centipoise. Examples of suitable thickening agents nonexclusively include: mono or diesters of 1) polyethylene glycol of formula: HO—(CH$_2$CH$_2$O)$_n$H, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

Any of a variety of commercially available secondary conditioners, such as volatile silicones, which impart additional attributes, such as gloss to the hair are suitable for use in this invention. In one embodiment, the volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids.

Any of a variety of commercially available humectants, which are capable of providing moisturization and conditioning properties to the personal cleansing composition, are suitable for use in the present invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2) polyalkylene glycol of the formula: HO—(R"O)$_b$—H, wherein R" is an alkylene group having from about 2 to about 3 carbon atoms and b is an integer of from about 2 to about 10; 3) polyethylene glycol ether of methyl glucose of formula CH$_3$—C$_6$H$_{10}$O$_5$—(OCH$_2$CH$_2$)$_n$—OH, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 1100XL" and is present in an amount, based upon the total weight of the composition, from about 0 to about 0.5 percent or from about 0.05 percent to about 0.25 percent.

Suitable preservatives include Quaternium-15, available commercially as "Dowicil 200" from the Dow Chemical Corporation of Midland, Mich., and are present in the composition in an amount, based upon the total weight of the composition, from about 0 to about 0.2 percent or from about 0.05 percent to about 0.10 percent.

The methods of the present invention may further comprise any of a variety of steps for mixing or introducing one or more of the optional components described hereinabove with or into a composition comprising a hydrophobically-modified material and/or an anionic surfactant either before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising a hydrophobically-modified material and/or an anionic surfactant.

The reduced irritation compositions produced via the present invention are preferably used as or in personal care products such as shampoos, washes, baths, gels, lotions, creams, and the like. As discussed above, applicants have discovered unexpectedly that the instant methods allow for the formulation of such personal care products having reduced irritation to the skin and/or eyes and desirable foaming characteristics.

According to certain other preferred embodiments, the present invention provides methods for cleansing skin or hair with reduced irritation thereto comprising the step of contacting the skin or hair of a mammal with a reduced irritation composition comprising an anionic surfactant and a hydrophobically-modified material capable of binding the anionic surfactant thereto.

Any conventional means for contacting mammalian skin and/or hair can be used according to the present invention. In certain preferred embodiments, the contacting step comprises applying a reduced irritation composition of the present invention to human skin and/or human hair.

The cleansing methods of the present invention may further comprise any of a variety of additional, optional steps associated conventionally with cleansing hair and skin including, for example, lathering, rinsing steps, and the like.

EXAMPLES

The following Trans-Epithelial Permeability ("TEP") and Tensiometry tests are used in the instant methods and in the following Examples. In particular, as described above, the TEP test is used to determine when a composition is a reduced irritation composition according to the present invention, and the Tensiometry test may be used to determine the suitability of a particular hydrophobically-modified material for binding surfactant thereto.

Trans-Epithelial Permeability Test ("TEP Test"):

Irritation to the eyes and/or skin expected for a given formulation is measured in accordance with the Invittox Protocol Number 86, the "Trans-epithelial Permeability (TEP) Assay" as set forth in Invittox Protocol Number 86 (May 1994), incorporated herein by reference. In general, the ocular and/or skin irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the $EC_{50}$ (the concentration of test material that causes 50% of maximum dye leakage, i.e., 50% damage to the permeability barrier). Higher scores are indicative of milder formulas.

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma; causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

Tensiometry Titration Test:

A well-known method to measure the surface tension of surfactant solutions is the Wilhelmy plate method (Holmberg, K.; Jonsson, B.; Kronberg, B.; Lindman, B. *Surfactants and Polymers in Aqueous Solution*, Wiley & Sons, p. 347). In the method, a plate is submerged into a liquid and the downward force exerted by of the liquid on the plate is measured. The surface tension of the liquid can then be determined based on the force on the plate and the dimensions of the plate. It is also well known that by measuring the surface tension over a range of concentrations the critical micelle concentration (CMC) can then be determined.

There are commercially available Wilhelmy plate method instruments. In the following examples, a Kruss K12 Tensiomter (Kruss USA, Mathews, N.C.) with a platinum Wilhelmy plate used to determine the surface tension of each sample over a range of concentrations. The test can be run either forward or reverse. In either case, a sample vessel contains some initial solution in which the Wilhelmy plate measures the surface tension. Then a second solution is dosed into the sample vessel, stirred, and then probed again with the Wilhelmy plate. The solution initially in the sample vessel before the titration begins, into which the second solution is dosed, will be referred to hereinafter as the initial solution, and the solution that is dosed into the sample vessel during the titration will be referred to hereinafter as the dosing solution, in accordance with the convention used by Kruss USA.

In the forward titration, the concentration of the initial solution is lower than the concentration of the dosing solution. In this example during forward titration tests, the initial solution was HLPC grade water (Fischer Scientific, NJ), with no sodium trideceth sulfate. The dosing solution was a solution of sodium trideceth sulfate and HLPC grade water (Fischer Scientific, NJ) with a concentration of 5750 mg/L of sodium trideceth sulfate. A large stock solution, 4L, of the dosing surfactant solution was prepared before hand; sodium trideceth sulfate (Stepan Company, Northfield, Ill.) was added to HLPC grade water (Fischer Scientific, NJ) to a concentration of 5750 mg/L.

At the beginning of the forward titration, 50 ml of initial solution was added to the sample vessel. The surface tension of this initial solution was measured, and then a volume of the dosing solution was added to the sample vessel. The solution was stirred for at least 5 minutes, before the next surface tension measures was taken. All titrations were run from 0 mg/L to at least 3500 mg/L of sodium trideceth sulfate, which is well beyond the CMC of all samples. A test run according to this procedure is here after referred to as a Forward Titration Tensiomtry Test.

Alternatively in the reverse titration, the concentration of the initial solution is higher than the concentration of the dosing solution. During the reverse titration tests of the following examples, the dosing solution was HLPC grade water (Fischer Scientific, NJ), which had no surfactant, 0 mg/L. The full concentration formulas (for example, those in Table 1) were diluted with HLPC grade water (Fischer Scientific, NJ) to a dilution of approximately 5% wt. This 5% diluted solution was then added to the sample vessel and was the initial solution. The surface tension of this initial solution was measured, and then a volume of the dosing solution was added to the sample vessel. The solution was stirred for at least 5 minutes, before the next surface tension measures was taken. This dosing, stirring, and then measuring was repeated until the dilution reached at least 0.0008%. A Test run according to this procedure is here after referred to as a Reverse Titration Tensiomtry Test.

Figure 2:
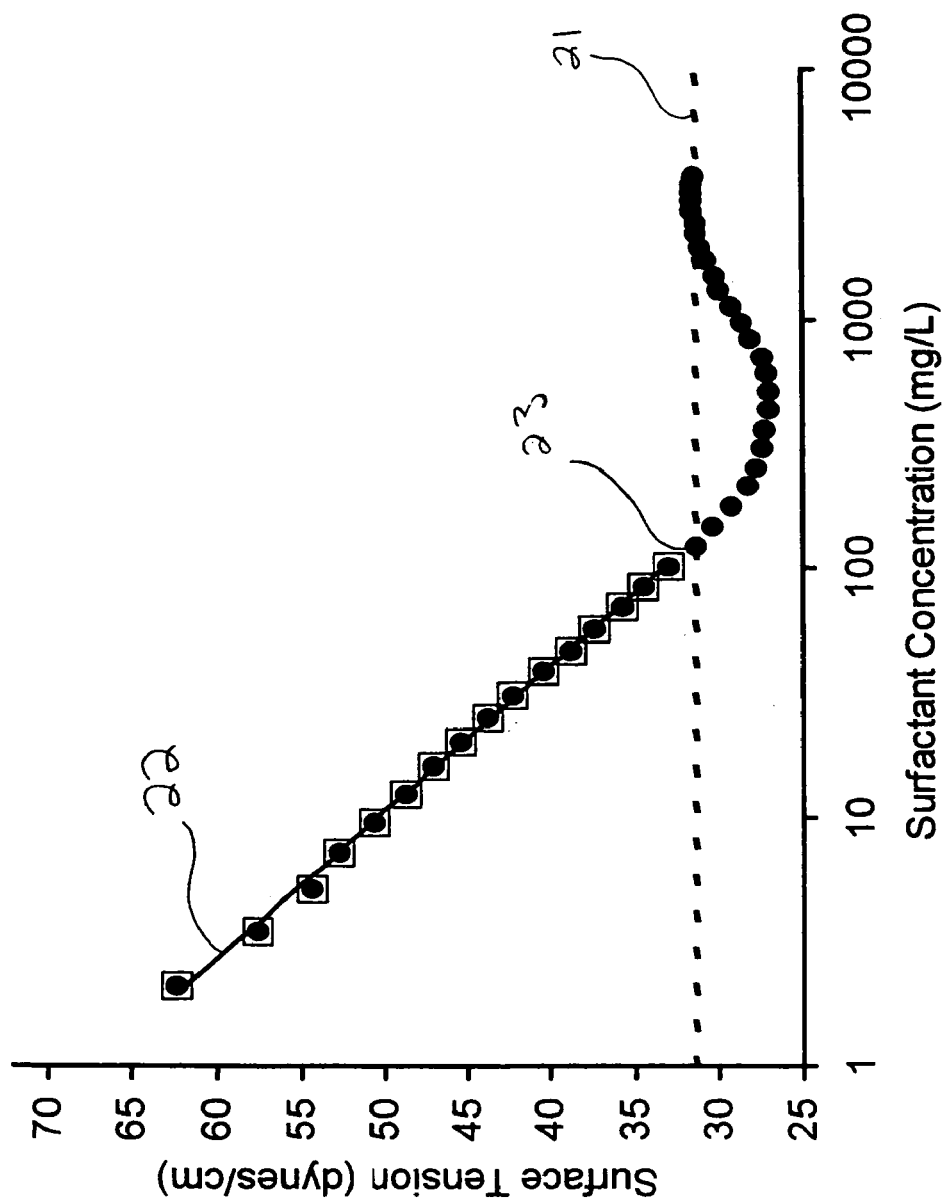
FIG. 2 is a graphical depiction of the tensiometry data and CMC measurement calculated for a composition according to one embodiment of the present invention.
Figure 3:
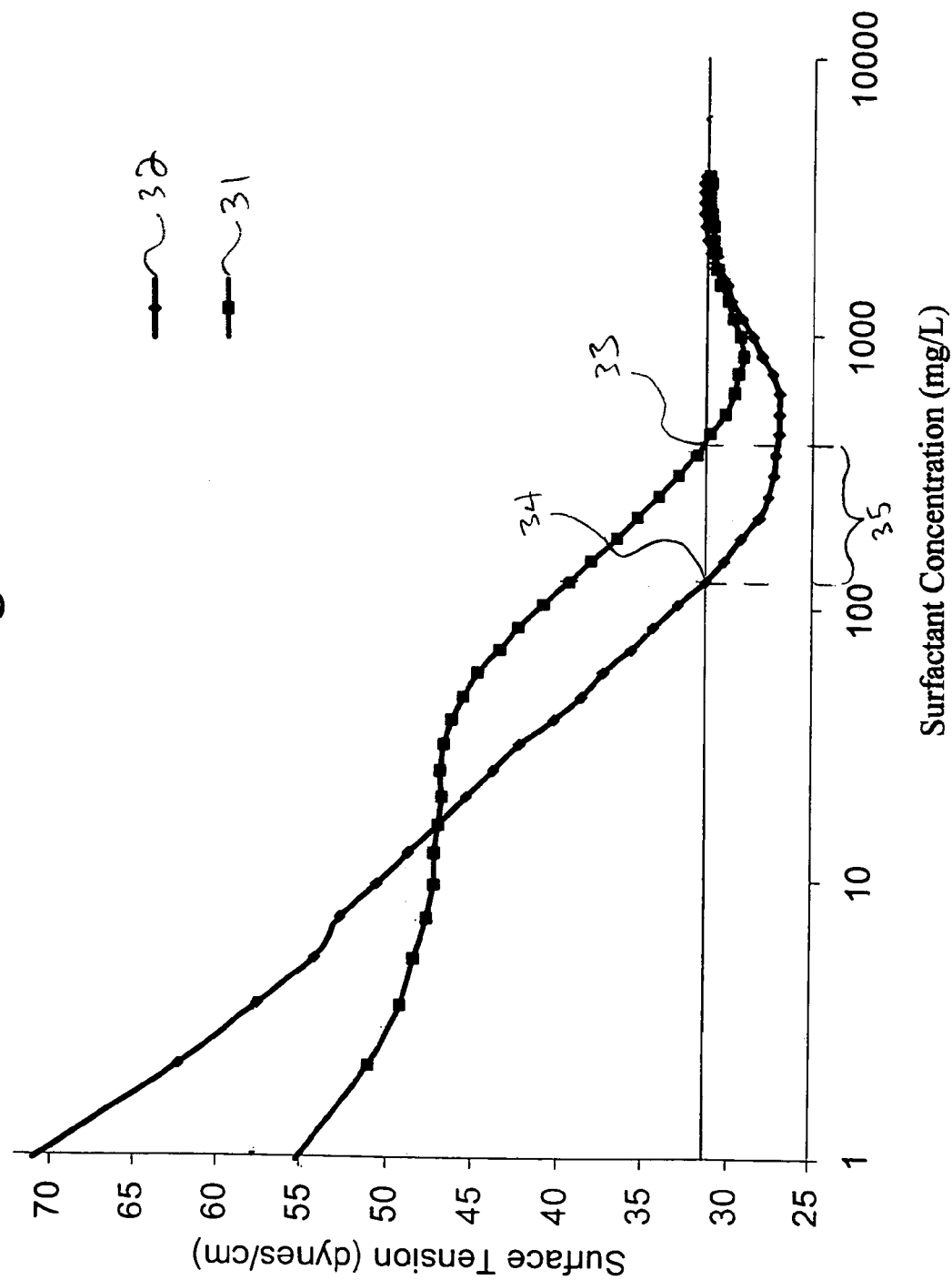
FIG. 3 is a graphical depiction of the tensiometry data and Delta CMC measurement calculated for a composition according to one embodiment of the present invention.

From the raw tensiomtry data, the CMC was determined for each sample in the following manner. First, the equation for a horizontal line was fitted to the portion of the data at high concentrations, i.e. concentrations above the nadir of the graph and well into the region where the surface tension is essentially constant, as shown, for example, in FIG. 2 as line 21. Then, the equation for a straight line is fit to the data at lower concentrations having a surface tension above the horizontal line derived previously, as shown, for example, in FIG. 2 as line 22. The intersection of these two lines/equations 23 was then defined as the CMC for that sample.

Examples 1–4

Preparation of Cleansing Compositions

The cleansing compositions of Examples 1 through 4 were prepared according to the materials and amounts listed in Table 1.

TABLE 1*

| Tradename | INCI Name | 1 | 2 | 3 | 4 |
|---|---|---|---|---|---|
| PEG 8000 (100%) | PEG 8000 | 1.800 | — | — | — |
| Polyox WSR 205 (100%) | PEG-14M | — | 1.800 | — | — |
| Carbopol ETD 2020 (100%) | Carbomer | — | — | 1.800 | — |
| Carbopol AQUA SF1 (30%) | Acrylates Copolymer | — | — | — | 6.000 |
| Tegobetaine L7V (30%) | Cocamidopropyl Betaine | 9.330 | 9.330 | 9.330 | 9.330 |
| Monateric 949J (30%) | Disodium Lauroamphodiacetate | 2.000 | 2.000 | 2.000 | 2.000 |
| Cedepal TD403LD (30%) | Sodium Trideceth Sulfate | 10.000 | 10.000 | 10.000 | 10.000 |
| Glycerin 917 (99%) | Glycerin | 1.900 | 1.900 | 1.900 | 1.900 |
| Polymer JR-400 | Polyquaternium-10 | 0.140 | 0.140 | 0.140 | 0.140 |
| Dowicil 200 | Quaternium-15 | 0.050 | 0.050 | 0.050 | 0.050 |
| Versene 100XL | Tetrasodium EDTA | 0.263 | 0.263 | 0.263 | 0.263 |
| Sodium Hydroxide solution (20%) | Sodium Hydroxide | — | 0.500 | 0.500 | 0.500 |
| Citric Acid solution (20%) | Citric Acid | 0.500 | — | — | — |
| Water | Water | qs | Qs | qs | qs |

*expressed in % w/w

The compositions of Table 1 were prepared as follows:
Water (50.0 parts) was added to a beaker. The polymer, (PEG 8000 in Example #1, Polyox WSR 205 in Example #2, Carbopol ETD 2020 in Example #3 and Carbopol Aqua SF1 in Example #4) was added to the water with mixing. The following ingredients were added thereto independently with mixing until each respective resulting mixture was homogenous:
Tegobetaine L7V, Monateric 949J, Cedepal TD403LD, Glycerin 917, Polymer JR400, Dowicil 200, and Versene 100XL. The pH of the resulting solution was then adjusted with either a 20% Citric Acid solution (Example 2) or a 20% Sodium Hydroxide solution (Examples 1, 3, 4) until a final pH of about 6.3 to 6.6 was obtained. The remainder of the water was then added thereto.

Mildness Comparison of Cleansing Compositions: The compositions prepared in accordance with Examples 1–4 were tested for mildness in accordance with the above TEP Test. The results of these tests are listed below in Table 2:

TABLE 2

Mildness Comparison

| Example | TEP value |
|---|---|
| Example 1 | 3.64 ± 1.01 |
| Example 2 | 3.69 ± 0.98 |
| Example 3 | 4.08 ± 0.18 |
| Example 4 | 4.93 ± 0.32* |

*= Statistically Significantly Different (95% CI)

This Example demonstrates that not all materials are capable of mitigating skin and eye irritation of a cleansing surfactant composition equally.

Examples 5–8

Preparation of Tensiometry Titration Compositions

The compositions of Examples 5 through 9 were prepared according to the materials and amounts listed in Table 3:

TABLE 3*

| Tradename | INCI Name | 5 | 6 | 7 | 8 | 9 |
|---|---|---|---|---|---|---|
| PEG 8000 (100%) | PEG 8000 | — | 0.050 | — | — | — |
| Polyox WSR 205 (100%) | PEG-14M | — | — | 0.050 | — | — |
| Carbopol ETD 2020 (100%) | Carbomer | — | — | — | 0.050 | — |
| Carbopol AQUA SF1 (30%) | Acrylates Copolymer | — | — | — | — | 0.167 |
| Sodium Hydroxide solution (20%) | Sodium Hydroxide | — | — | — | As needed | As needed |
| DI Water | DI Water | Qs | Qs | Qs | Qs | Qs |

*expressed in % w/w

The compositions of Table 3 were prepared as follows: HPLC grade water (50.0 parts) was added to a beaker. The polymer, (PEG 8000 in Example #1, Polyox WSR 205 in Example #2, Carbopol ETD 2020 in Example #3 and Carbopol Aqua SF1 in Example #4) was added to the water with mixing. The pH of the resulting solution was then adjusted with a 20% Sodium Hydroxide solution (as needed) until a final pH of about 7.0 was obtained. The remainder of the water was then added thereto.

Critical Micelle Concentration Values: The compositions prepared in accordance with Examples 5–9 were tested for Critical Micelle Concentration (CMC) values using the forward titration tensiomtry experiment. The initial solution was 50 ml of one of the Examples 5 through 9. The dosing solution was 5750 mg/L of sodium trideceth sulfate in HPLC grade water. 42 dose were preformed, which increased the sodium trideceth concentration from 0 mg/L in the initial solution up to 3771 mg/L at the final measurement.

The results of this test are listed below in Table 4:

TABLE 4

Critical Micelle Concentration Comparison

| Example | CMC value (mg/L) | Delta CMC (mg/L) |
|---------|------------------|------------------|
| Example 5 | 125 | — |
| Example 6 | 83 | −42 |
| Example 7 | 122 | −3 |
| Example 8 | 169 | 44 |
| Example 9 | 400 | 275 |

The CMC is the surfactant concentration (in this example sodium trideceth sulfate) at which free micelles begin to form. At surfactant concentration below the CMC, no surfactant exist as free micelles, while at concentrations above the CMC free micelles are present in solution. In Example 5, the CMC was measured without any polymer and found to be 125 mg/L. Also shown in Table 4 is the Delta CMC associated with the composition of Example 5 (without additional material). In Example 6, with PEG 8000, the measured CMC was 83, which is below the CMC of that in Example 0.5, only surfactant no polymer.

In Example 7, the addition of Polyox WSR 205 to the solution resulted an insignificant change in the CMC compared to the solution without additional material, Example 5. However the addition of Carbopol ETD 2020 did have a significant effect on the CMC, increasing the CMC from 124 mg/L without additional material up to 169 mg/L; this represents the second largest Delta CMC. Example 8, Carbopol SF-1, possess the highest CMC, and the largest Delta CMC.

This example shows that the addition of certain materials to the solution can change the CMC of the surfactant in solution. An increase in the CMC of the solutions suggests that the onset of free micelles formation occurs at higher concentrations. In Example 5, free micelles begin to form at 124 mg/L of trideceth sulfate, while in Example 9 free micelle do not begin to form until 400 mg/L of trideceth sulfate.

We believe that the shift in the CMC to higher concentration with the addition of certain materials (i.e., Example 8 and 9) occurs because surfactant associates with said material, thereby reducing the free monomer concentration. The free monomer concentration is reduced proportional to the amount of surfactant associated with the material. The magnitude of the Delta CMC suggests the amount of surfactant that the material is capable of associating with, or the efficiency of the material in associating surfactant.

The addition of PEG 8000 (Example 1 and 6) resulted in the lowest TEP score, most irritating, and the lowest CMC. The addition of Polyox WSR 205 (Example 2 and 7) resulted in the second lowest TEP score, and the second lowest CMC. The addition of Carbopol ETD 2020 (Example 3 and 8) resulted in the second highest TEP score, and the second largest shift in the CMC. The addition of Carbopol Aqua SF-I (Example 4 and 9) resulted in the highest TEP score, and the largest shift in the CMC. Surprisingly, we discovered a relationship/correlation between the magnitude of the CMC shift caused by the addition of a material and the mildness of the composition. The addition of a material or materials that results in a larger shift of the CMC results in improved mildness of the composition. The addition of a material that causes a sufficient increase in CMC results in a composition with reduced irritation.

In Example 9, the concentration of Carbopol Aqua SF-1 was 500 mg/L, and the CMC was 400 mg/L of sodium trideceth sulfate, while the CMC of sodium trideceth sulfate without SF-1 was 125 mg/L. Therefore, the material of Example 9 associated with 275 mg of sodium trideceth sulfate per every 500 mg of material, or 0.183 g of sodium trideceth sulfate per 1.0 g of Aqua SF-1. The efficiency of a material to associate surfactant is the Delta CMC per mass of the material. A material with a higher efficiency will associate more surfactant and will produce a larger Delta CMC.

Examples 10–15

Preparation of Cleansing Compositions

The cleansing compositions of Examples 10 through 15 were prepared according to the materials and amounts listed in Table 5.

TABLE 5*

| | INCI Name | 10 | 11 | 12 | 13 | 14 | 15 |
|---|---|---|---|---|---|---|---|
| Carbopol Aqua SF-1 (30%) | Acrylates Copolymer | — | 0.900 | 2.700 | 3.600 | 4.500 | 6.000 |
| Atlas G-4280 (72%) | PEG-80 Sorbitan Laurate | 4.580 | 4.580 | 4.580 | 4.580 | 4.580 | 4.580 |
| Tegobetaine L7V (30%) | Cocamidopropyl Betaine | 11.330 | 11.330 | 11.330 | 11.330 | 11.330 | 11.330 |
| Cedepal TD403LD (30%) | Sodium Trideceth Sulfate | 20.000 | 20.000 | 20.000 | 20.000 | 20.000 | 20.000 |
| Glycerin 917 (99%) | Glycerin | 1.900 | 1.900 | 1.900 | 1.900 | 1.900 | 1.900 |
| Polymer JR-400 | Polyquaternium-10 | 0.140 | 0.140 | 0.140 | 0.140 | 0.140 | 0.140 |
| Dowicil 200 | Quaternium-15 | 0.050 | 0.050 | 0.050 | 0.050 | 0.050 | 0.050 |

TABLE 5*-continued

| | INCI Name | 10 | 11 | 12 | 13 | 14 | 15 |
|---|---|---|---|---|---|---|---|
| Versene 100XL | Tetrasodium EDTA | 0.263 | 0.263 | 0.263 | 0.263 | 0.263 | 0.263 |
| Water | Water | qs | qs | Qs | qs | qs | qs |

*expressed in % w/w

Each of the compositions of Table 5 was independently prepared as follows: Water (50.0 parts) was added to a beaker. For examples 11 through 15, Carbopol Aqua SF-1 was added to the water with mixing. (For Example 10, this step was omitted.) The Atlas G-4280 was then added thereto with mixing. For examples 10–15, the following ingredients were then added thereto independently with mixing until each respective resulting mixture was homogenous: Tegobetaine L7V, Cedepal TD403LD, Glycerin 917, Polymer JR400, Dowicil 200, and Versene 100XL. The pH of the resulting solution was then adjusted with either a 20% Sodium Hydroxide solution or a 20% Citric Acid solution until a final pH of about 6.3 to 6.6 was obtained. The remainder of the water was then added thereto.

Mildness Comparison of Cleansing Compositions: The compositions prepared in accordance with Examples 10–15 were then tested for mildness in accordance with the above TEP Test. Table 6 lists the TEP value of the composition of each Example:

TABLE 6

Mildness Comparison

| Example | TEP value | Delta TEP Value |
|---|---|---|
| Example 10 | 1.46 ± 0.26 | — |
| Example 11 | 2.68 ± 0.28 | 1.22 |
| Example 12 | 2.85 ± 0.51 | 1.39 |
| Example 13 | 2.74 ± 0.18 | 1.28 |
| Example 14 | 3.34 ± 0.83 | 1.88 |
| Example 15 | 3.26 ± 0.39 | 1.80 |

As shown in Example 10, the composition containing a relatively high amount of anionic surfactant (6.0% active) without the Carbopol Aqua SF1 recorded a relatively low TEP value and thus was considered to be irritating. However, upon the addition of the Carbopol Aqua SF1 thereto as shown in Example 11, the TEP score was improved. Examples 12 to 15 further showed that as the amount of Carbopol Aqua SF-1 added to the composition was increased, the TEP values for those respective compositions were generally concomitantly improved. Also shown in Table 6 is the Delta TEP score relative to the comparable composition, Example 10 (without any Carbopol Aqua SF-1).

These Examples indicated that the presence of the Carbopol Aqua SF1 significantly improved the skin and eye mildness of the compositions via binding of surfactant thereto, and that such mildness generally improved as the amount of the copolymer was increased. The majority of the increase in the TEP score (68%) occurs with the addition of only 0.9% Carbopol Aqua SF-1, Example 10.

Critical Micelle Concentration Comparison of Cleansing Compositions: The compositions prepared in accordance with Examples 10–15 were then tested for Critical Micelle Concentration in accordance with the above Reverse Titration Tensiometry Test. Table 7 lists the CMC values of the composition of each Example:

TABLE 7

Critical Micelle Concentration Comparison

| Example | CMC value (mg/L) | Delta CMC (mg/L) |
|---|---|---|
| Example 10 | 48 | — |
| Example 11 | 65 | 17 |
| Example 12 | 136 | 88 |
| Example 13 | 377 | 329 |
| Example 14 | 370 | 322 |
| Example 15 | 398 | 350 |

This series of examples, 10–15 shows that as the amount of Carbopol Aqua SF-1 was increased from 0 to 6% (0 to 1.8% active), the Delta CMC increased to higher values. While not bound by any particular theory, we attribute this increase in the Delta CMC that results by increasing concentration of Carbopol Aqua SF-1 to the ability of the Carbopol Aqua SF-1 to bind surfactant thereto. As more Carbopol Aqua SF-1 is added to the composition (from Example 10 to 15) more surfactant is bound thereto. Since surfactant that is bound to the Carbopol Aqua SF-1 does not contribute to the free monomer concentration, the CMC is shifted to higher values.

Similarly, as shown in Table 6, the mildness (TEP values) of the composition generally increases with increasing concentrations of Carbopol Aqua SF-1. Again with Examples 10–15, we find a correlation between the increase in CMC and Delta CMC and the improved mildness (TEP/Delta TEP scores) of the composition.

What is claimed is:

1. A method of reducing the irritation associated with a personal care composition comprising at least one anionic surfactant, the method comprising combining a hydrophobically-modified material capable of binding a surfactant thereto with at least one anionic surfactant comprising sodium trideceth sulfate to produce a reduced irritation personal care composition having a Delta CMC of at least about 80.

2. The method of claim 1 wherein said reduced irritation composition has a Delta TEP of at least about 1.

3. The method of claim 2 wherein said reduced irritation composition has a Delta TEP of at least about 1.2.

4. The method of claim 3 wherein said reduced irritation composition has a Delta TEP of at least about 1.8.

5. The method of claim 1 wherein said reduced irritation composition has a Delta CMC of at least about 300.

6. The method of claim 1 wherein said hydrophobically-modified material is selected from the group consisting of hydrophobically-modified acrylic polymers, hydrophobically-modified cellulosics, hydrophobically-modfied starches, and combinations of two or more thereof.

7. The method of claim 6 wherein said hydrophobically-modified material comprises a hydrophobically-modified acrylic polymer.

8. The method of claim 7 wherein said hydrophobically-modified acrylic polymer is derived from at least one unsaturated carboxylic acid monomer; at least one hydrophobic monomer; a hydrophobic chain transfer agent comprising one or more alkyl mercaptans, thioesters, amino acid-mercaptan-containing compounds, peptide fragments, or combinations thereof; a cross-linking agent; and, optionally, a steric stabilizer; wherein the amount of said unsaturated carboxylic acid monomer is from about 60% to about 98% by weight based upon the total weight of said unsaturated monomers and said hydrophobic monomer.

9. The method of claim 1 wherein said at least one anionic surfactant further comprises at least one other anionic surfactant selected from the group consisting of alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof.

10. The method of claim 1 wherein said reduced irritation composition comprises from about 0.1 to about 12.5% anionic surfactant.

11. The method of claim 10 wherein said reduced irritation composition comprises from about 0.5 to about 8.5% anionic surfactant.

12. The method of claim 11 wherein said reduced irritation composition comprises from about 1 to about 8% anionic surfactant.

13. The method of claim 1 wherein said reduced irritation composition further comprises one or more materials selected from the group consisting of nonionic, amphoteric, and cationic surfactants, pearlescent agents, opacifying agents, thickening agents, secondary conditioners, humectants, chelating agents, colorants, fragrances, preservatives, and pH adjusting agents.

14. A method of reducing the irritation associated with a personal care composition comprising at least one anionic surfactant, the method comprising combining a hydrophobically-modified acrylic polymer material capable of binding a surfactant thereto with at least one anionic surfactant comprising sodium trideceth sulfate to produce a reduced irritation personal care composition having a Delta TEP of at least about 1.2 and a Delta CMC of at least about 80, said reduced irritation composition further comprising at least one material selected from the group consisting of nonionic, amphoteric, and cationic surfactants, pearlescent agents, opacifying agents, thickening agents, secondary conditioners, humectants, chelating agents, colorants, fragrances, preservatives, pH adjusting agents, and combinations of two or more thereof.

15. A method of cleansing skin or hair with reduced irritation thereto comprising the step of contacting the skin or hair of a mammal with a reduced irritation composition produced according to claim 1.

* * * * *